US006436050B2

(12) United States Patent
Garrison et al.

(10) Patent No.: US 6,436,050 B2
(45) Date of Patent: Aug. 20, 2002

(54) REMOVABLE GRIP FOR ULTRASOUND PROBE

(75) Inventors: Brevard S. Garrison, Reading; Michael G. Verga, Newton; Julie A. Beberman, North Easton, all of MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/752,483

(22) Filed: Jan. 2, 2001

Related U.S. Application Data

(62) Division of application No. 09/318,912, filed on May 26, 1999.

(51) Int. Cl.$^7$ ................................................ A61B 8/00
(52) U.S. Cl. ....................................................... 600/459
(58) Field of Search ................................ 600/437, 459; 73/631–632

(56) References Cited

U.S. PATENT DOCUMENTS

| | | | | |
|---|---|---|---|---|
| 4,483,344 A | * | 11/1984 | Atkov et al. | 600/459 |
| 4,898,177 A | * | 2/1990 | Takano et al. | 600/459 |
| 5,671,747 A | * | 9/1997 | Connor | 600/459 |
| 5,792,059 A | * | 8/1998 | Furia et al. | 600/459 |
| 5,897,503 A | * | 4/1999 | Lyon et al. | 600/459 |

* cited by examiner

*Primary Examiner*—Francis J. Jaworski
(74) *Attorney, Agent, or Firm*—John Vodopia

(57) ABSTRACT

A removable grip for an ultrasound probe. The grip may be an integrated or unitary hand-held device having a circular or C-shaped cross-section that, when located at a predetermined operative position on the probe, removably surrounds a substantial portion of the probe to provide an exterior shape and size optimal for a desired application. The probe is generally an elongated instrument having proximal and distal ends and an external casing that is grasped by a sonographer. An ultrasound transducer is generally disposed at the distal end and a cord for transferring data and power typically extends from the proximal end of the probe. The grip includes proximal and distal ends and, in one disclosed aspect, a channel for receiving the cord. The channel is defined by opposing edges of the grip that longitudinally extend between the proximal and distal ends. The channel extends through the grip from an exterior surface to an interior surface of the grip. The grip has an attachment feature that enables the grip to be detachably secured to the probe casing when in the operative position such that manual forces applied to the grip to position the probe against a patient do not cause the grip to detach from the probe.

5 Claims, 6 Drawing Sheets

REMOVABLE GRIP FOR ULTRASOUND PROBE

CROSS REFERENCE TO RELATED APPLICATION

This is a divisional of copending application Ser. No. 09/318,912 filed on May 26, 1999.

BACKGROUND OF THE INVENTION

1. Field of the Invention

The present invention relates generally to ultrasound probes and, more particularly, to removable grips for ultrasound imaging probes.

2. Related Art

The use of ultrasound for medical imaging is well-known. Since its introduction, advances in technology and clinical practice have made ultrasound a leading medical diagnostic imaging modality. Ultrasound provides high-resolution real-time imaging without the use of ionizing radiation which is required for other techniques such as X-ray imaging. In addition, modern ultrasound equipment is relatively inexpensive and portable. This cost-effectiveness and portability has resulted in the widespread application of ultrasound imaging to observe a considerable range of physical conditions and to identify many types of disorders. For example, ultrasound imaging is commonly used in such clinical applications as obstetrics and gynecology, general abdominal imaging, vascular imaging and cardiology. This latter application, which is of significance in the present application, is referred to as echocardiography.

Non-invasive echocardiography is performed generally using a transthoracic ultrasound imaging probe. Conventional transthoracic ultrasound imaging probes are generally elongated devices having an ultrasound transducer located on the distal end of the device body. Ultrasound probes are generally constructed of a hard plastic casing to facilitate cleaning. Typically, the probe is maneuvered so that the transducer is positioned adjacent to an external location on the body where acoustic imaging is facilitated by the underlying tissue. In cardiac imaging, these locations, referred to as imaging windows, are typically in the vicinity of the rib cage.

There are four primary echocardiographic imaging windows: the suprasternal, subcostal, parasternal and apical windows. The appropriateness of each imaging window depends upon the structures, functions and conditions to be diagnosed as well as the type and size of the patient. Each imaging window provides an opportunity to image a specific portion or characteristic of the cardiac structures and/or functions depending on the portion of the heart which is nearest the selected imaging window, the angle of the probe at that window, and the intervening structures which may interfere with imaging the desired cardiac structures. In addition, the utility of certain windows is limited by the size and condition of the patient. Accordingly, specific windows are used to diagnose specific imaging conditions and disorders of specific patients.

When performing transthoracic echocardiographic procedures, the patient is generally lying horizontally on his or her left side. While the patient lies still in an appropriate position, the sonographer applies the transducer to a predetermined imaging window on the patient's body. The transducer must be positioned at the correct location and in the correct orientation at the selected imaging window to successfully transmit the ultrasound signals at the proper angle so as to obtain clear and accurate cardiac images.

To place the probe in the proper position, the sonographer must maintain complete control over the probe throughout the echocardiograph procedure. This often requires the sonographer to apply a significant gripping force to the probe casing. Two techniques are commonly used. Left-handed scanning calls for holding the ultrasound probe with the left hand while manipulating the ultrasound imaging system controls with the right hand. Conversely, right-handed scanning calls for using the right hand to control the ultrasound probe while manipulating the imaging system with the left hand. Typically, a right-handed sonographer is positioned behind the horizontally-positioned patient. The sonographer must reach completely around the right side of the patient to properly position the ultrasound probe at one of the ultrasound imaging windows. The gripping force that must be applied by the sonographer to push and hold the probe in the proper location and orientation is significant in such an awkward position. In other situations, the sonographer may have to work in environments even more awkward, such as operating rooms, intensive care units, etc., as well as with patients that have difficulty remaining still, such as children and injured patients. It is not uncommon for the sonographer to repeat many procedures to ensure that the obtained images are accurate representations of the cardiac condition and not artifacts due to improper placement or orientation of the probe.

In addition, a large percentage of patients on which echocardiography is performed are obese. With these patients, the sonographer must apply a significant axial force to the probe to compress and displace layers of fat. Furthermore, the use of coupling gel to obtain a clearer image interferes with the sonographer's capability to securely hold and control the ultrasound probe when the coupling gel migrates from the transducer onto the gripping surfaces of the probe casing.

Conventional probes generally have surface features to enable the sonographer to establish the proper orientation of the probe. For example, some ultrasound probes have curves, scallops or ridges, while other probes have a localized feature such as a line, rib, flute, button or some other feature on one side of the transducer. Although such orientation-related features of conventional ultrasound probes may provide some incidental assistance to the sonographer to maintain control over the probe, these features provide insignificant and insufficient assistance, ancillary to the purpose of establishing proper orientation of the probe.

What is needed, therefore, is a means for assisting a sonographer's control of an ultrasound probe in various imaging scenarios, including different relative positions of the sonographer and the patient, varying patient conditions, and the presence or absence of coupling gel. Also, a range of gripping styles and hand sizes should be accommodated. The probe should be comfortable to hold and easily controllable with minimal gripping force to reduce fatigue and the occurrence of occupational injuries.

SUMMARY OF THE INVENTION

The present invention is an apparatus and a method related to a removable grip for an ultrasound probe. The grip is a hand-held device that, when located at a predetermined operative position on the probe, provides an exterior shape and size optimal for manually grasping during a desired application. In one aspect, the grip has an attachment feature that enables the grip to be detachably secured to the probe casing at the operative position such that manual forces applied to the grip to position the probe against a patient do not cause the grip to detach from the probe. The probe is generally an elongated instrument having proximal and distal ends and an external casing that is grasped by a sonographer. An ultrasound transducer is generally disposed at the distal end and a cord for transferring data and power typically extends from the proximal end of the probe.

In one aspect of the invention, a hand-held grip adapted to removably surround a substantial portion of an ultrasound probe is disclosed. The grip includes proximal and distal ends and a channel for receiving the cord. The channel is defined by opposing edges of the grip that longitudinally extend between the proximal and distal ends. The channel extends through the grip from an exterior surface to an interior surface of the grip so as to define a C-shaped cross-section of the grip.

In one embodiment, the channel has a width larger than a diameter of the cord, enabling the cord to pass freely through the channel. In another embodiment, the grip is flexible and the grip has an unbiased position in which the width of the channel is smaller than the diameter of the cord and a biased position in which the width of the channel is larger than the diameter of the cord. In this embodiment, a force must be applied to cause the cord to travel through the channel.

The attachment feature may take on any number of configurations. In addition, the probe may include one or more features on the probe casing that may be utilized in embodiments of the attachment feature to facilitate secure, yet detachable attachment of the grip. Thus, as used herein, the term "attachment feature" broadly covers any feature, configuration, or other aspect of the grip that facilitates a secure, yet detachable, attachment of the grip to the probe when the grip is located in the operative position on the probe. For example, in one embodiment, the probe is contoured so that it is narrower at its proximal and distal ends and wider in a mid-region between the proximal and distal ends. Here, the grip includes a tapered region on the interior surface. The tapered region tapers from a wider cross-sectional region toward the proximal end of the grip to a narrower cross-sectional region toward the distal end of the grip. The narrower cross-sectional region of the grip has an unbiased position that interoperates with the mid-region of the probe to prevent the grip from moving toward the proximal end of the probe.

In another embodiment, the exterior casing includes a raised region having a predetermined shape that provides an abutment surface substantially orthogonal to the surface of the exterior casing and the longitudinal axis of the probe. One or both of the opposing edges that form the grip channel have formed therein a recess configured to receive the raised region and to contact the abutment surface. As the grip is translated over the exterior casing, the grip is placed in an unbiased state as the raised region travels through the grip channel. When the recess in the one or both opposing edges receives the raised region, the grip attains a less-biased or unbiased state, resulting in the grip being detachably secured around a substantial portion of the probe.

The grip may also be detachably secured to the probe in a configuration in which the casing has at least one protrusion, and the attachment feature includes at least one corresponding indentation that is adapted to interlock with the protrusion of the casing when the grip is located in its operative position on the probe. Alternatively or additionally, the grip may have at least one protrusion and the casing at least one interlocking indentation. The protrusion of the grip is adapted to interlock with the indentation of the casing to detachably secure the grip to the probe.

In yet another embodiment, screw threads are formed on the external casing of the probe. In this embodiment, the attachment feature includes screw threads formed on the interior surface of the grip constructed and arranged to threadedly interoperate with the screw threads formed on the casing. In one particular embodiment, the grip includes a notch in the interior surface to align the grip with a detent on the probe thereby preventing the grip from rotating relative to the probe.

In one particular embodiment, interlocking mechanisms are disposed on the opposing edges of the grip that form the channel. The interlocking mechanisms are adapted to interlock with each other to enable the grip to be detachably secured to the probe.

In another aspect, the grip is not detachably secured to the probe. Rather, it is held in its operational position around the probe by manually applied axial forces toward the distal end of the probe. In one particular embodiment, the probe is contoured to have a cross-section at the proximal that is less than a cross-section at the distal end, with the external casing widening at a substantially constant rate between the proximal and distal ends. To interoperate with such an external casing, an interior surface of the grip is contoured to have a cross-section at the proximal that is less than a cross-section at the distal end, with the interior surface widening at a substantially constant rate between the proximal and distal ends of the grip such that the tapered interior surface contacts the exterior casing of the probe when the grip is in its operational position around the probe.

In many of the above or other configurations, the probe is nonaxisymmetric and the interior surface of the grip is also nonaxisymmetric to prevent the grip from rotating relative to the probe. The relative position of the grip with respect to the probe may be maintained by abutting surfaces. The probe may have an abutting surface and the interior surface of the grip may have a corresponding abutting surface. Contact of the abutting surfaces of the grip and probe prevents axial motion of the grip toward the distal end of the probe.

In another aspect of the invention a method for removably surrounding a unitary, C-shaped, hand-held grip around a substantial portion of an ultrasound probe is disclosed. The grip comprises proximal and distal ends and a channel defined by opposing edges of the grip that longitudinally extend between the proximal and distal ends. The channel extends through the grip, from an exterior surface to an interior surface of the grip. The probe is constructed and arranged substantially the same as described above. The method comprises the steps of removably receiving the cord through a channel extending along the grip and reversibly translating the grip from a location in which the cord is positioned with the grip to a location in which the grip surrounds the substantial portion of the probe.

Advantageously, the grip of the present invention, being larger than the probe and having some or all of the attributes mentioned above, enables an administering sonographer to maintain control over the ultrasound probe during transthoracic and other ultrasound imaging procedures while applying minimal gripping force. As a result, the sonographer is required to use less gripping force throughout the procedure, preventing fatigue and enabling the sonographer to perform ultrasound imaging procedures for longer periods of time without loss of control. Importantly, the grip enables the sonographer to efficiently obtain accurate ultrasound images from desired ultrasound viewing windows regardless of the position of the patient, the location of the sonographer relative to the patient, and whether the sonographer uses right- or left-handed techniques.

Further features and advantages of the present invention, as well as the structure and operation of various embodiments of the present invention, are described in detail below with reference to the accompanying drawings. In the drawings, like reference numbers indicate like or functionally similar elements.

BRIEF DESCRIPTION OF THE DRAWINGS

This invention is pointed out with particularity in the appended claims. The above and further advantages of this invention may be better understood by referring to the following description when taken in conjunction with the accompanying drawings, in which:

DETAILED DESCRIPTION

The present invention is an apparatus and a method related to a removable grip for an ultrasound probe. The grip removably attaches to an exterior surface of an ultrasound probe. When positioned at a predetermined operative position on the probe, the grip surrounds a substantial portion of the probe to provide a gripping surface that is comfortable to hold and easily controllable with minimal gripping force.

The probe is generally an elongated device having proximal and distal ends and an external casing that is grasped by a sonographer. A transducer array is generally disposed at the distal end and a cord for transferring data and power typically extends from the proximal end of the probe. The grip is generally an elongated cylindrical device having openings at its proximal and distal ends. To attach the grip, the probe's proximal end is inserted into the distal opening of the grip and the grip is translated in an axial direction relative to the probe toward the distal end of the probe until the grip is located in its operative position on the probe. Removal of the grip is achieved through a reverse relative axial movement.

Figure 1:
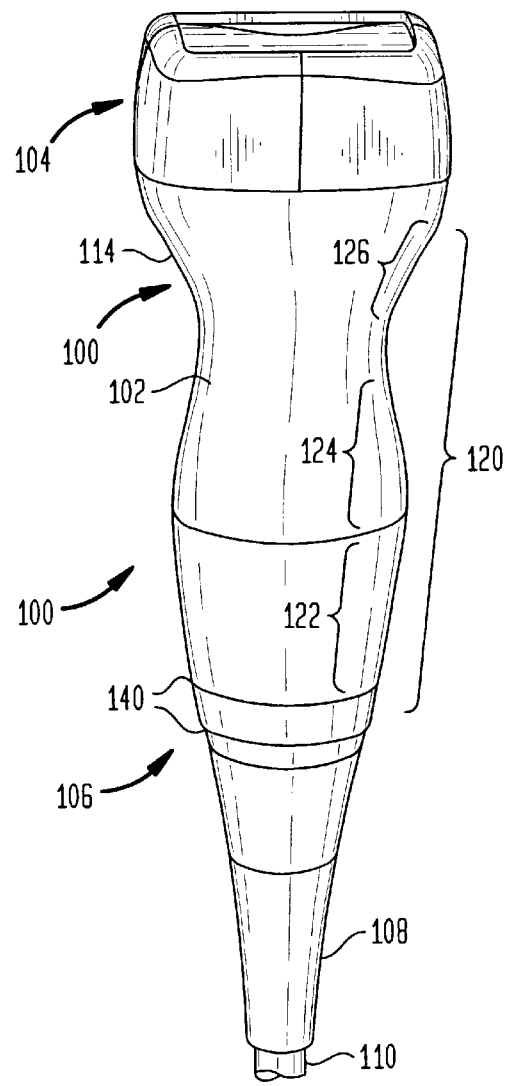
FIG. 1 is a side perspective view of one exemplary ultrasound probe suitable for use with the present invention.

FIG. 1 is a side perspective view of an exemplary ultrasound probe suitable for use with the present invention. In this illustrative embodiment, a probe 100 includes an external casing 102 which houses well-known internal components. At a nose or distal end 104 of probe 100 is an ultrasound transducer and a transducer lens (not shown) which is placed against a patient's body to obtain ultrasound images. Attached to a tail or proximal end 106 of probe 100 is a cable assembly 108 to which is attached a cord 110 for carrying power and data signals between probe 100 and an ultrasound imaging system (not shown). The terms "distal end" and "proximal end" will be used herein to refer to those portions of the specified element that are toward the nose and tail, respectively, of probe 100.

Figure 2:
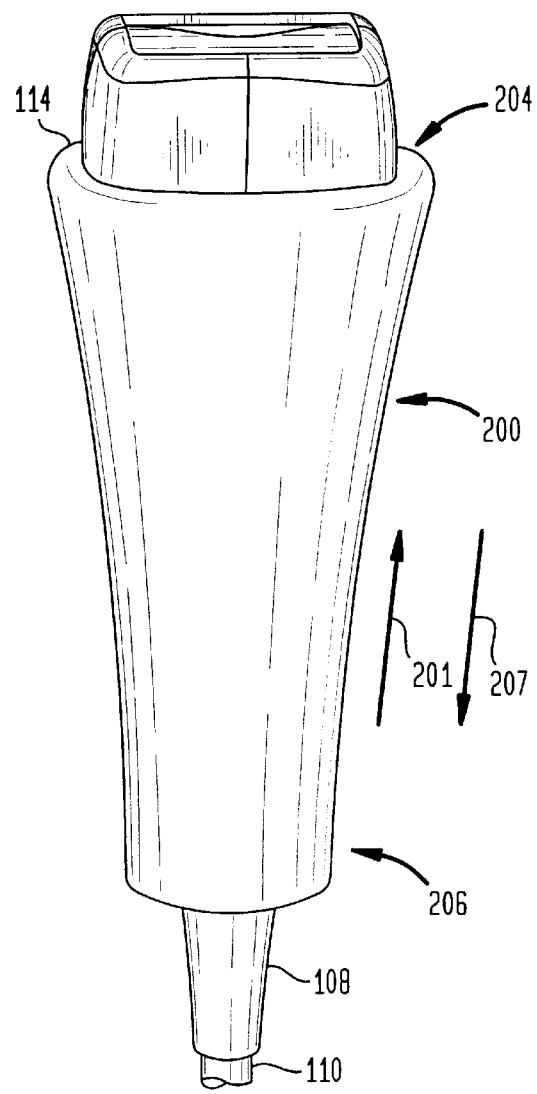
FIG. 2 is a side perspective view of one embodiment of the removable grip of the present invention in its operative position on the ultrasound probe of FIG. 1.
Figure 3:
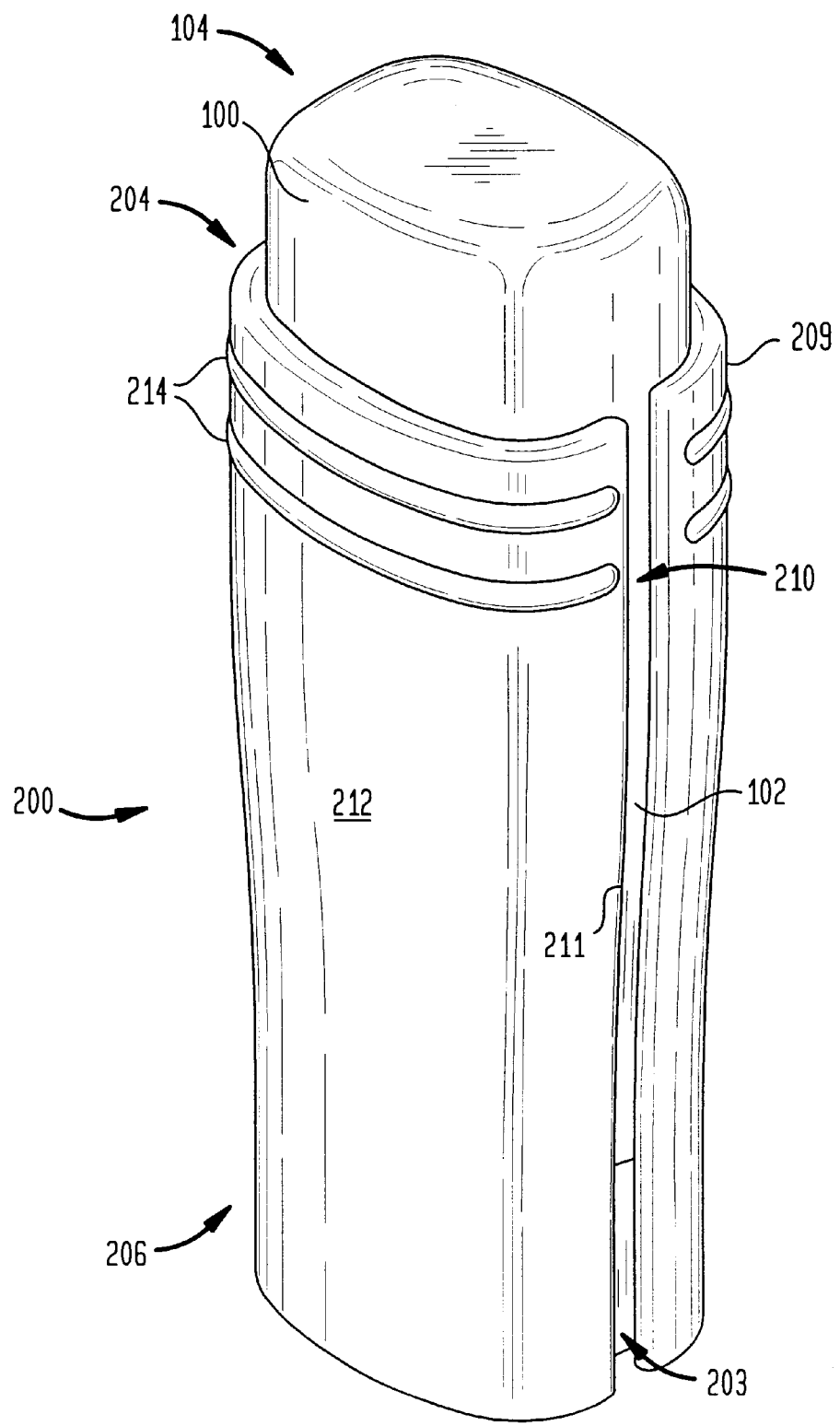
FIG. 3 is a perspective view of the embodiment of the removable grip shown in FIG. 2.
Figure 4:
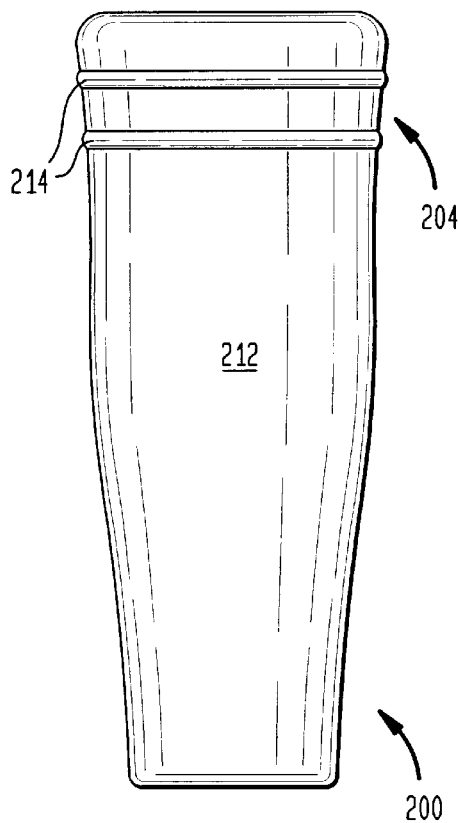
FIG. 4 is a side view of the grip of FIG. 3.
Figure 5:
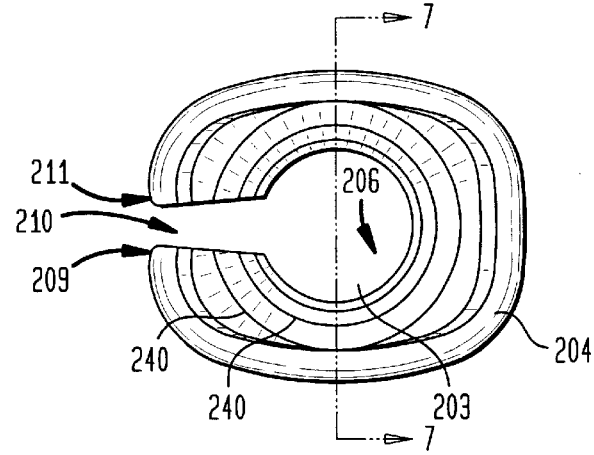
FIG. 5 is a front view of the grip of FIG. 3.
Figure 6:
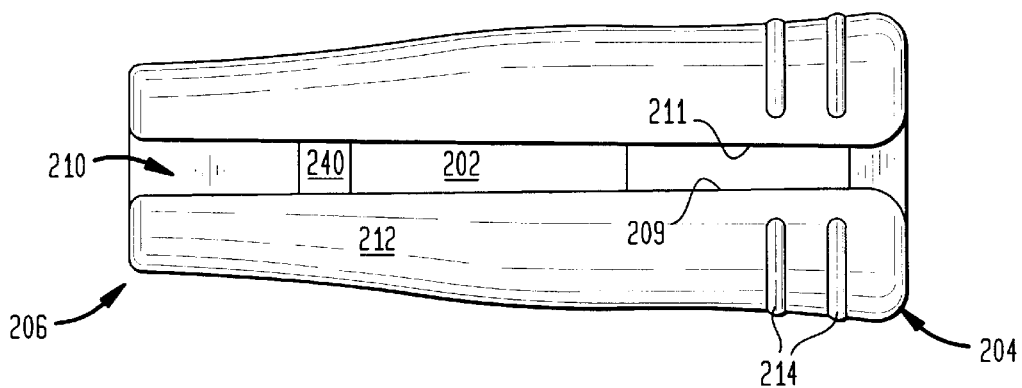
FIG. 6 is a side view of the grip of FIG. 3.
Figure 7:
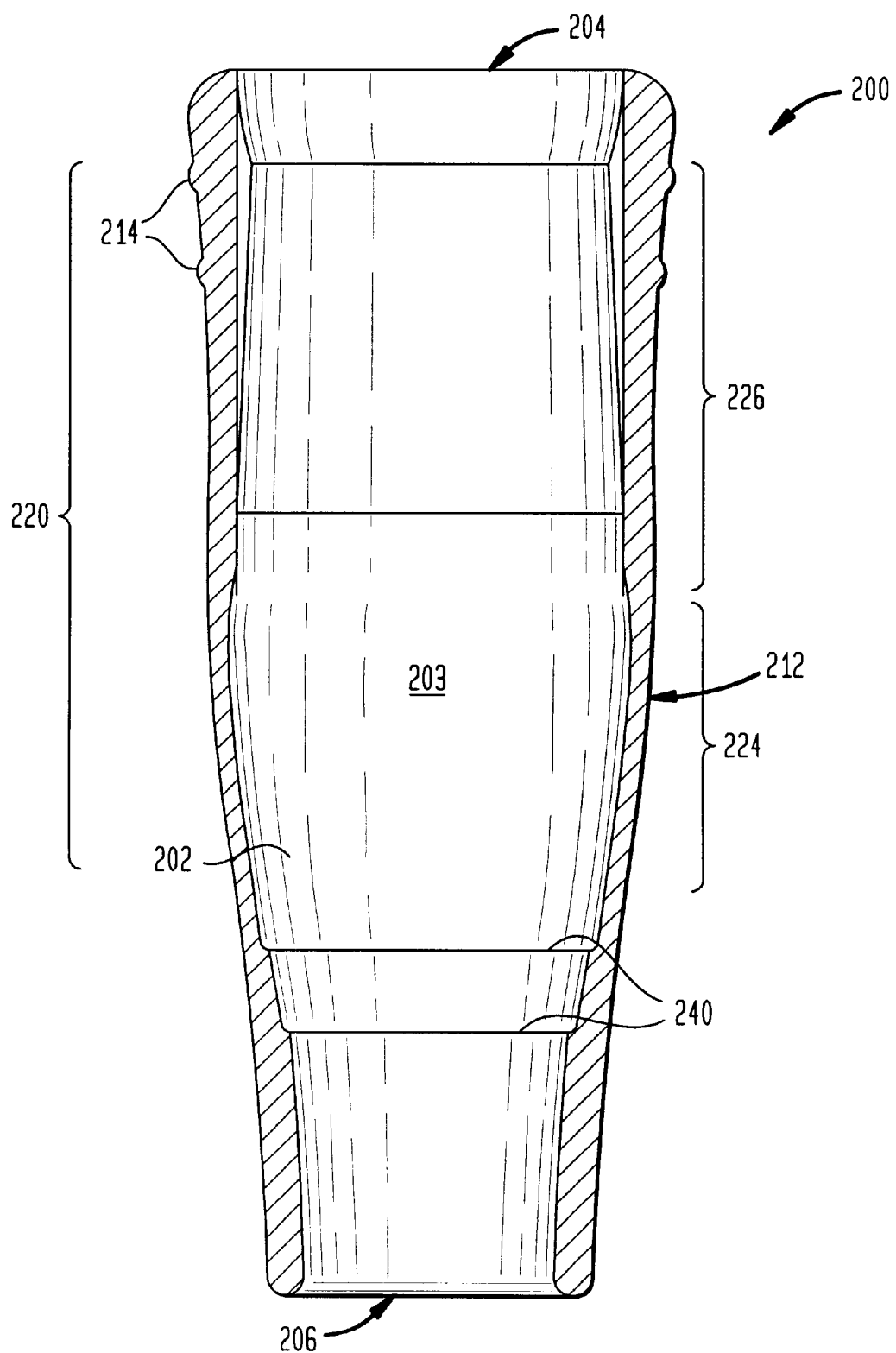
FIG. 7 is a cross-sectional side view of the grip of FIG. 3 taken along the line 7—7 of FIG. 5 showing a tapered region and abutting surfaces.

FIG. 2 is a perspective view of one embodiment of an ultrasound probe removable grip of the present invention installed in an operative position on ultrasound probe 100. FIG. 3 is a perspective view of a removable grip installed on probe 100. FIGS. 4, 5 and 6 are left side, front and right side views of the removable grip illustrated in FIGS. 2 and 3. FIG. 7 is a cross-sectional side view of the removable grip taken along cross-section line 7—7 of FIG. 5.

Grip 200 has an outside cross-sectional diameter and exterior shape sufficient to enable probe 100 (with grip 200 attached) to be comfortably held by a sonographer. The exterior shape and size of grip 200 may be configured to accommodate any desired application. For example, in one embodiment, grip 200 has an exterior cross-sectional diameter and length ("size and shape") that are optimal for the performance of a particular ultrasound imaging procedure. Alternatively, other factors such as type of technique or training, size of sonographer's hand, ergonomic objectives, etc. may be considered in the determination of the exterior size and shape of the exterior surface of grip 200. Thus, when grip 200 is attached to and surrounds probe 100, a sonographer can maintain control of the probe when performing echocardiographic and other ultrasound procedures appropriate for probe 100.

As noted, grip 200 removably attaches to probe 100. It may be used temporarily and, when desired, can be easily and quickly attached to or detached from probe 100. Such attachment and detachment is achieved through a relative axial displacement of grip 200 relative to probe 100; that is, grip 200 is slid over probe 100. For reasons described in detail below, grip 200 is configured to slide over probe 100 in a direction as shown by arrow 201; that is, from proximal end 106 toward distal end 104 of probe 100. Conversely, grip 200 is detached and removed from probe 100 by translating grip 200 in a direction 207 relative to probe 100.

It is envisioned that a sonographer may desire the use of grip 200 during one portion of a procedure and not for others. To ensure that grip 200 is continually available for use and to facilitate incorporation of grip 200 into a procedure, grip 200 assumes two positions: A detached position wherein grip 200 is located at some position on cord 110, and an attached position wherein grip 200 is in an operative position surrounding probe 100.

For example, when performing an echocardiographic procedure at the subcostal window, probe distal end 104 is required to be oriented toward the heart at such an angle that probe 100 is positioned substantially lengthwise against the patient's body. Absence of grip 200 facilitates this procedure. Immediately thereafter a different viewing window such as the apical window may be used. Here, use of grip 200 assists in the application of the requisite pressure to position probe 100 at an angle that is less shallow than used at the subcostal window. An additional benefit stemming from the capability to have grip 200 quickly and easily removed from probe 100 is that it allows casing 102 and grip 200 to be cleared between ultrasound imaging procedures.

Grip 200 is generally cylindrical; that is, it is generally an elongated, tubular member having an exterior surface as described above and an interior hollow region 203 defined by an interior surface 202. Grip 200 has a distal end 204 for receiving probe 100 when grip 200 is attached to probe 100, and a proximal end 206 through which cable 108 extends when grip 200 is operatively attached to probe 100.

It is anticipated that circumstances may arise that require the use of more than one grip in a relatively short period of time and, in particular, during a single sonographic procedure with a single patient. For example, if a sonographer is having difficulty in obtaining an image using one grip, a second grip having a different shape and size may provide the needed assistance. In other circumstances, a sonographer may experience reduced grip strength, increased pain or other condition that may be rectified or alleviated by substituting a grip currently installed on probe 100 with a different grip having a different exterior size and shape. In addition, a second sonographer may be involved in the administration of a sonographic procedure, requiring the use of a second grip appropriate for the second sonographer. For example, when an image cannot be obtained or the integrity of the obtained image is in question, a second sonographer may be involved to obtain those particular images. A grip appropriate for the second sonographer facilitates the accurate attainment of such images. As such, in accordance with one aspect of the invention grip 200 is one of a set of grips. The set of grips may include grips of various sizes and shapes, all of which may be used with a single probe 100 due to a common interior configuration described below.

To facilitate the fast and easy substitution of such grips, certain embodiments of grip 200 preferably have a C-shaped cross-section. Referring to FIGS. 3, 5 and 6, a channel 210 is formed within such embodiments of grip 200. Channel 210 is defined by opposing edges 209 and 211 extending longitudinally along the length of grip 200 between proximal end 206 and distal end 204. Channel 210 extends from exterior surface 212 to interior surface 202, as best shown in FIGS. 5 and 6. Such a configuration, described in greater detail below, enables grip 200 to be removed from cord 110 when in the detached position around cord 110, and allows for the rapid incorporation of a different grip 200 into a sonographic procedure simply by passing cord 110 through channel 210 in the appropriate direction.

Thus, grip 200 is initially installed by receiving cord 110 through channel 210. Grip 200 is then translated toward probe distal end 104 to its detachably secured operative position around probe casing 102. Grip 200 may be uninstalled by applying a requisite axial force to grip 200 in direction 207. Such a force causes grip 200 to detach from casing 102 and translate in direction 207 relative to probe 100 to a position beyond probe proximal end 106. Grip 200 is completely removed by pulling cord 110 through channel 210 from interior region 203 to the exterior of grip 200. An additional benefit associated with the complete removal of grip 200 from probe 100 is that grip 200 can be cleaned separately from probe 100. This also permits the same grip 200 to be used on multiple probes 100 having similar external casing 102. Also, removal of grip 200 allows disposable embodiments of grip 200 to be discarded and replaced by another grip 200.

Preferably, channel 210 is sized to allow cord 110 to pass therethrough as well as to retain cord 110 within interior region 203 of grip 200, preventing grip 200 from inadvertently separating from cord 110. In one embodiment, the width of channel 210 along a portion of channel 210 is slightly less than a diameter of cord 110. In such an embodiment, grip 200 is flexible and has a shape memory. Grip 200 is capable of being biased so that channel 210 widens enough to receive cord 110. After cord 110 is received into region 203, grip 200 resumes its unbiased position and channel 210 narrows, thereby preventing the unassisted passage of cord 110 through channel 210. Such assistance may be provided with minimal manual force applied to cord 110 and grip 200 to cause cord 110 to pass through channel 210.

In another embodiment, the width of channel 210 is slightly larger than the diameter of cord 110. Although in this embodiment cord 110 has a greater likelihood of accidentally separating from grip 200, cord 110 generally is retained within grip 200 because in a slackened state cord 110 flexes or pleats. The flexure prevents a sufficient length of cord 110 to simultaneously align with and pass through channel 210. It should be apparent that any other number of relative states of channel diameter and channel width may be implemented.

In certain aspects of the illustrative embodiment of the present invention, grip 200 includes an attachment feature that enables grip 200 to be detachably secured to probe 100. In certain aspects of the invention the attachment feature interoperates with features of probe casing 102 to enable grip 200 to be maintained in its operative position during normal use of probe 100. In other aspects of the invention, the attachment feature may not interoperate with any particular feature or features, but interoperates generally with exterior casing 102.

Since probe 100 is just one of many probe configurations to which embodiments of grip 200 may be attached, embodiments of the attachment feature may take on any number of configurations, some of which are described herein. In addition, probe 100 may include one or more features on exterior casing 202 that may be utilized in embodiments of the attachment feature to facilitate secure yet removable attachment of grip 200. Thus, as used herein, the term "attachment feature" broadly covers any feature, configuration, or other aspect of grip 200 that facilitates a secure yet detachable attachment of grip 200 to probe 100.

In the illustrative embodiment shown in FIGS. 3–7, the attachment feature comprises tapered regions formed within interior surface 202 of grip 200 so as to complement and interoperate with tapered regions of probe 100 to achieve the desired retention of grip 200 in its operative position. Referring again to FIG. 1, casing 102 has a tapered region 120 in which a cross-section of casing 102 tapers from a first narrower region 122 adjacent to proximal end 106 to a wider mid-region 124. Casing 102 then tapers from mid-region 124 to a second narrower region 126 adjacent distal end 104. Referring to FIGS. 5–7, the attachment feature includes complementary tapered region 220 formed on interior surface 202 having a configuration that enables grip 200 to interlock with probe tapered regions 120 when grip 200 is installed at the operative position on probe 100. As best shown in FIG. 7, tapered region 220 on interior surface 202 has an inner cross-section that causes interior surface 202 to taper from a narrower region 226 adjacent distal end 204 to an adjacent wider region 224. The rate and extent of such tapers corresponds to those of probe 120.

As grip 200 is translated from around cord 110 toward distal end 104 of probe 100, narrower region 226 of grip 200 passes freely over the first narrower region 122 adjacent proximal end 106 of probe 100 until it reaches the wider mid-region 124 of probe 100. As grip 200 is axially translated further toward distal end 104, wider mid-region 124 pushes outward narrower region 226 of grip 200 so that grip 200 is biased outward. This enables narrower region 226 of grip 200 to pass over wider mid-region 124 of probe 100 until the narrower region 226 of grip 200 reaches second narrower region 126 adjacent distal end 104 of probe 100 where grip 200 returns to its unbiased position. In the unbiased position, grip 200 is fully inserted in its operative position on probe 100, with narrower region 226 of grip 200 aligned with second narrower region 126 adjacent distal end 104 of probe 100. Grip 200 is held in this unbiased position by the adjacent wider mid-region 124 of probe 100 which prevents the narrower region 226 of grip 200 from freely passing back toward proximal end 106 of probe 100 without application of some force to overcome the shape memory of grip 200.

As can be appreciated, the axial manual force applied to grip 200 during operation can vary greatly. In particular, axial force in direction 201 toward distal end 104 of probe 100 must be applied to place firmly probe 100 against the patient. As such, in the illustrative embodiment opposing abutting surfaces on the grip 200 and probe 100 prevent axial forces applied in direction 201 when grip 200 is in its operative position to cause grip 201 to continue to travel in direction 201 relative to probe 100 to a non-operative position.

In the illustrative embodiment, casing 102 includes two stepped surfaces 140 adjacent probe proximal end 106. Interior surface 202 of grip 200 has two similarly stepped surfaces 240 adjacent proximal end 206 of grip 200. When grip 200 is initially installed onto probe 100, grip 200 is translated axially relative to probe 100 until grip 200 is located at its operative position around probe 100. Upon reaching such an operative position, stepped surfaces 240 abut against stepped surfaces 140, preventing further travel of grip 200 toward distal end 104 of probe 100. As a result, abutting surfaces 140 and 240 prevent grip 200 from separating from probe 100 when an axial force is applied toward the distal end 106 of the probe 100. In alternative embodiments, additional features (described below) may be included in embodiments of the attachment feature.

Figure 8:
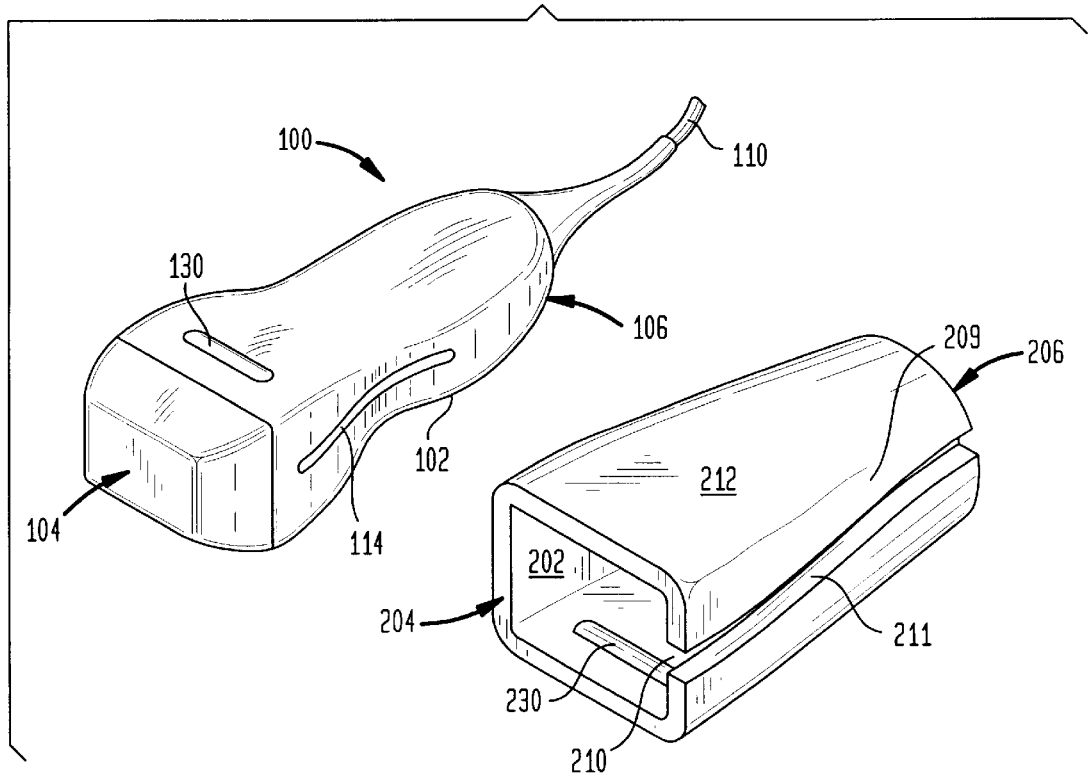
FIG. 8 is a perspective view of an embodiment in which the probe has a rib-shaped protrusion and the grip includes a corresponding indentation or opening.

FIG. 8 is a perspective view of an embodiment in which the probe has a rib-shaped protrusion and the grip includes a corresponding indentation or opening. In such an embodiment, the attachment feature includes a protrusion 130 on casing 102 and a corresponding indentations 230 formed on interior surface 202 of grip 200. The protrusion and indentation are complementary in shape including, for example, spherical, cylindrical, or rib-shaped configurations. To attach, grip 200 is translated toward distal end 104 of probe 100, as noted above. When grip 200 reaches protrusion 130 on casing 102, it is biased outward until protrusion 130 aligns with indentation 230. When protrusion 130 aligns with indentation 230, grip 200 resumes its unbiased position and is prevented from moving toward either distal 104 or proximal end 106 of probe 100, absent application of some predetermined force suitable for overcoming such a snap fit. Alternatively or additionally, interior surface 202 of grip 200 may be formed with a protrusion and casing 102 formed with an indentation.

Figure 9:
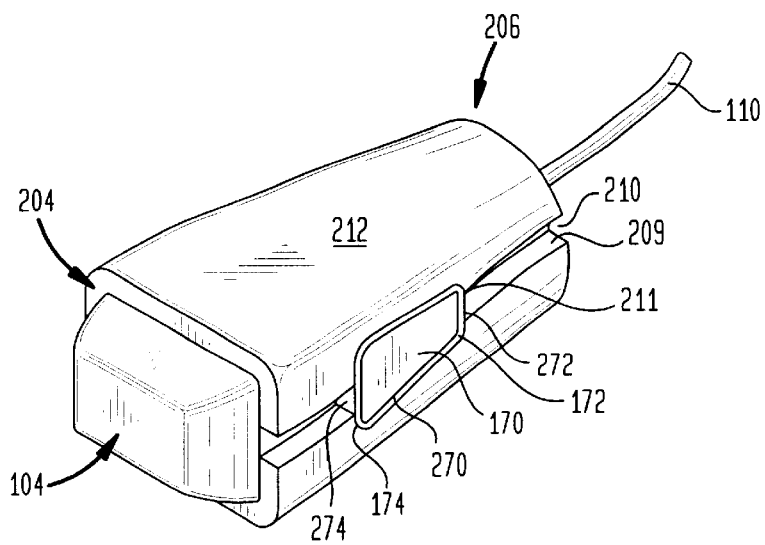
FIG. 9 is a perspective view of an embodiment of the grip surrounding the probe in which a raised portion of the probe is aligned with a correspondingly shaped opening formed by the edges of the channel of the grip.

FIG. 9 is a perspective view of an alternative embodiment of the attachment feature of the present invention wherein probe 100 has a raised portion 170 on probe casing 102. In this embodiment, grip 200 has a correspondingly-shaped channel opening 270 defined by edges 209 and 211 of grip 200. Grip 200 is secured to probe 100 through the interoperation of raised portion 170 on casing 102 and channel opening 270. In the illustrative embodiment, raised portion 170 has a narrower section 172 adjacent proximal end 106 and a wider section 174 adjacent distal end 104. Channel opening 270 is similar in shape to raised portion 170 with a narrower section 272 toward proximal end 206 and a wider section 274 toward distal end 204. As grip 200 is translated axially along probe 100 from proximal end 106 to distal end 104, channel 210 is initially separated by raised region 170. Continued relative translation causes additional separation until wider section 174 enters channel 210. When channel opening 270 aligns with raised portion 170, grip 200 snaps around raised portion 170 and resumes its unbiased position.

The interaction of channel opening 270 with raised portion 170 prevents both axial and rotational movement of grip 200 relative to probe 100.

Figure 10:
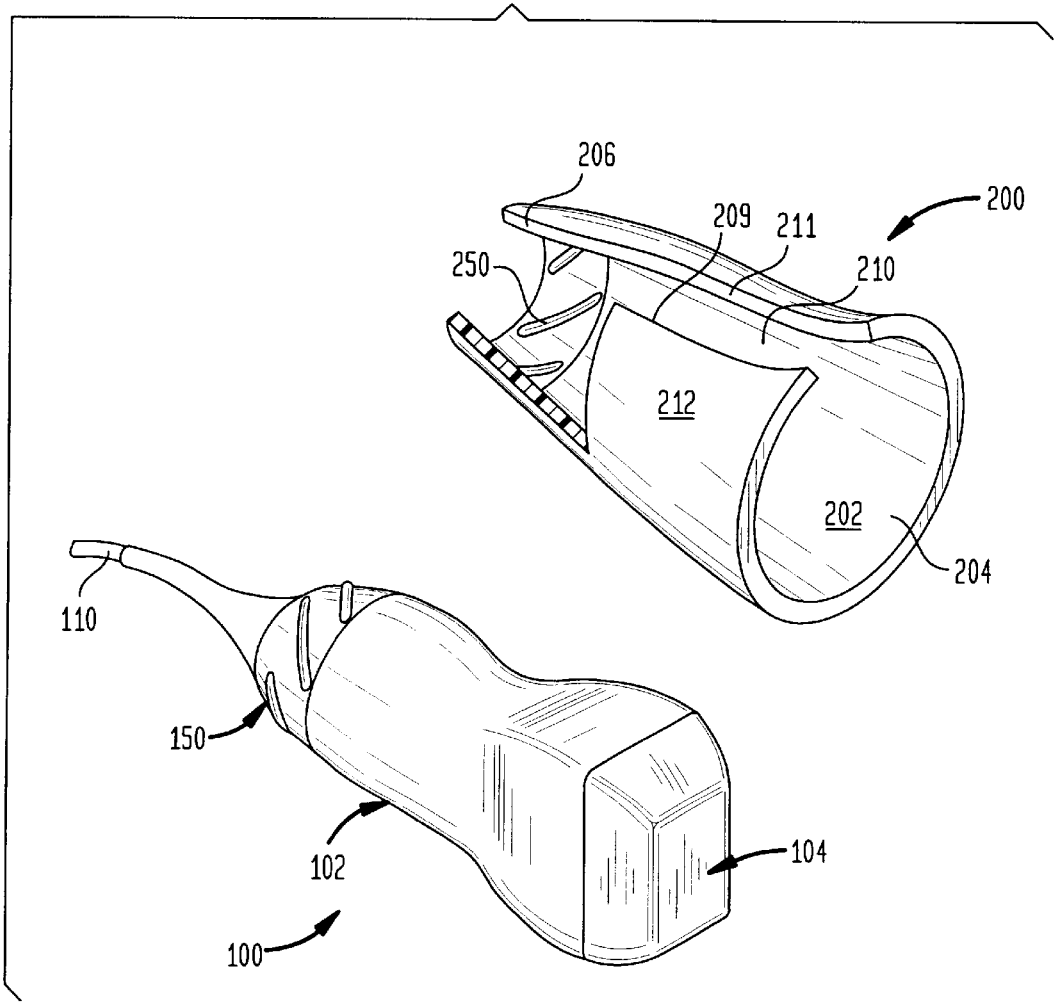
FIG. 10 is a perspective view of an embodiment in which the grip has screw threads formed on its interior surface and the probe has corresponding screw threads formed on the casing.

FIG. 10 is a perspective view of probe 100 and grip 200 incorporating another embodiment of the attachment feature of the present invention. In this embodiment, grip 200 is detachably mounted to probe 100 by interoperating screw threads. Interior surface 202 of grip 200 is formed with internal screw threads 250. Casing 102 is formed with external screw threads 150. Grip 200 is threadedly attached to probe 100. A detent may be provided at the distal end of the screw threads of probe 100 and a notch may be provided at the distal end of the screw threads of grip 200 to provide alignment of grip 200 with probe 100 for orientation purposes and to prevent grip 200 from rotating relative to probe 100 when a slight rotational force is applied.

It should be understood that other mechanisms and techniques for insuring grip 200 is detachably retained on probe 100 during normal operations may be used. For example, in one alternative embodiment, the attachment feature implements a friction or interference-type fit. In such an embodiment, the interior cross-section of interior surface 202 may be smaller than the exterior cross-section of casing 102. In such a configuration, grip 200 is biased outwardly to install it around casing 102 and is detachably secured to casing 102 by virtue of the force urging grip 200 to its smaller, unbiased position.

Figure 11:
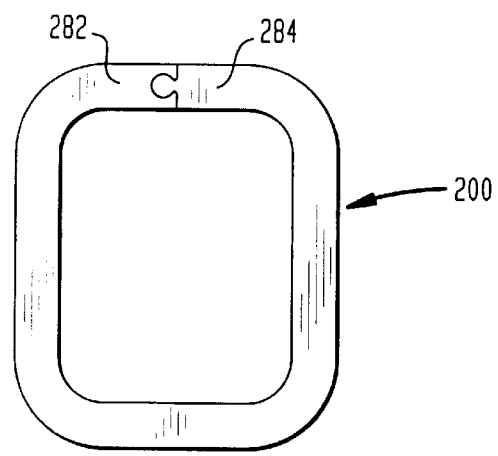
FIG. 11 is a cross-sectional view of an embodiment of the grip in which interlocking mechanisms are disposed on the edges of the channel.

An alternative embodiment of the attachment feature is implemented in embodiments of grip 200 that have a C-shaped cross-section as shown in FIGS. 3–7. This additional attachment feature, referred to as an interlocking mechanism, is shown in the cross-sectional view of FIG. 11. As shown in FIG. 11, opposing edges 209 and 211 have interlocking surfaces 282 and 284 forming a tongue and groove connection that easily mate. As one skilled in the art will find apparent other interlocking mechanisms may be used.

In another aspect, the grip 200 is not detachably secured to the casing 102. Rather, it is held in its operational position around the probe by manually applied axial forces toward the distal end of the probe 100. In one particular embodiment, the probe is contoured to have a cross-section at the proximal end that is less than a cross-section at the distal end, with the external casing widening at a substantially constant rate between the proximal and distal ends. To interoperate with such an external casing 102, an interior surface 202 of the grip is contoured to have a cross-section at the proximal end that is less than a cross-section at the distal end, with the interior surface widening at a substantially constant rate between the proximal and distal ends of the grip such that the tapered interior surface contacts the exterior casing of the probe when the grip is in its operational position around the probe.

In addition to the above features, casing 102 and interior surface 202 of grip 200 may take a variety of shapes. In certain embodiments, casing 102 of probe 100 and interior surface 202 of grip 200 are nonaxisymmetric as illustrated in FIGS. 1 and 2. This asymmetry prevents the grip 200 from rotating relative to probe 100.

In a further embodiment, grip 100 provides an orientation indication. When grip 200 is attached to the probe 100, grip 200 is aligned with an orientation feature of the probe 100. One type of orientation feature is the spline or ridge 114 shown in FIGS. 2 and 8. Ridge 114 fits within channel 210. Because channel 210 is aligned with probe 100, the orientation of probe 100 is readily ascertained by the sonographer by either seeing or touching channel 210, allowing the sonographer to easily properly orient probe 100 for performing imaging procedures. Grip 200 may also be color coded to correspond with a particular type or model of ultrasound probe 100.

Surface features on exterior surface 114 of grip 200 are desirable to prevent the sonographer's hand from slipping on the grip. In the embodiment shown in FIGS. 3–7, ribs 214 are provided orthogonal to the longitudinal axis of the grip. Other types of non-slip surfaces are also envisioned, such as a texturized surface with a plurality of bumps.

In alternative embodiments, grip 200 may take on other configurations that enable it to be attached and detached from probe 100. For example, in applications where easy removal is not required or desired, grip 200 may be a continuous, unitary member; that is, no channel 210 may be provided. In alternative embodiments, grip 200 may comprise two half-shells that are hinged with interlocking mechanisms at opposing longitudinal edges. These and other configurations that enable grip 200 to be removably secured to probe 100 and, when in an attached position, assist a sonographer in the performance of the intended procedure, are considered to be within the scope of the present invention.

Because grip 200 is removable, a single probe 100 may be used with grips of various materials. In one embodiment, the removable grip 200 withstands repeated applications of autoclaving, gas sterilization, liquid disinfection and other commonly used methods of sterilization. Materials suitable for a grip that can withstand such sterilization methods include polyetherimide, polyethersulfone, polyether ketone or metal, among others. The ability of grip 200 to withstand repeated applications of such sterilization techniques enables grip 200 to be reused.

Alternatively, grip 200 may be sterilizable, but not autoclavable. Sterilization techniques not requiring autoclaving include, application of a combination of hot water and various chemicals. Such a sterilizable material may have high chemical resistance as, for example, resistance without substantial deterioration for thirty days to materials encountered in the use environment which include isopropanol, glutaraldehyde, Clorox (5% sodium hypochlorite), and peracetic acid. Suitable materials for a sterilizable but not autoclavable grip include polyester, ABS, polycarbonate, and polycarbonate blend. Grip 200 may also be made from a material that cannot withstand sterilization and is disposable after use.

Preferably, the grip 200 is made from a substantially rigid material having a modulus of elasticity in the range of 250,000 to 1,200,000 psi. Grip 200 may also have a good tear resistance as, for example, tear strength of greater than 300 lb/in, ASTM D1922. Alternatively, grip 200 is constructed of more than one material with the interior surface 202 being a substantially rigid material having a modulus of elasticity in the range of 250,000 to 1,200,000 psi and exterior surface 212 being a substantially compressible material of low durometer in the range of Shore A3-65, ASTM D2240. The substantially rigid material of interior surface 202 provides for secure attachment of the grip 200 to casing 102 and the substantially compressible material of exterior surface 212 provides for a non-slip and comfortable hold for the sonographer.

Advantageously, various aspects and embodiments of grip 200 of the present invention enable an administering sonographer to maintain control over the ultrasound probe during transthoracic and other ultrasound imaging procedures while applying minimal gripping force. As a result, the sonographer is required to use less gripping force throughout the procedure, preventing fatigue and enabling the sonographer to perform ultrasound imaging procedures for longer periods of time without loss of control. Importantly, grip 200 enables the sonographer to efficiently obtain accurate ultrasound images from all ultrasound viewing windows regardless of the position of the patient, the location of the sonographer relative to the patient, and whether the sonographer uses right- or left-handed techniques.

While various embodiments of the present invention have been described above, it should be understood that they have been presented by way of example only, and not limitation. For example, although various embodiments have been disclosed in connection with certain aspects of the present invention, it should be understood that such embodiments may be combined in any combination that is non-conflicting or otherwise feasible. Thus, the breadth and scope of the present invention are not limited by any of the above-described exemplary embodiments, but are defined only in accordance with the following claims and their equivalents.

What is claimed is:

1. A method for arranging a grip with an ultrasound probe, the probe having a casing, a proximal end, a distal end, and a cord extending from the proximal end, and the grip comprising a semi-rigid tubular member constructed to include a c-shaped cross-section defining a channel, extending longitudinally along a length of the grip, comprising the steps of:

inserting the cord through the channel, wherein the grip construction further defines an interior space for substantially surrounding a portion of the probe, and wherein the interior surface of the body forming the interior space varies along the length of the grip; and translating the grip from around the cord to around the probe.

2. The method of claim 1, further comprising:

securing the grip to the probe.

3. The method of claim 1, further comprising:

detaching the grip from the probe;

translating the grip from around the probe to around the cord; and extracting the cord through the channel.

4. A probe for an ultrasound unit, the probe comprising:

a transducer;

a cable having a first end coupled to the transducer at a proximal end of the transducer and a second end coupled to a connector, the connector suited to couple the transducer to the ultrasound unit; and a grip having a body comprising an elongated semi-rigid tubular member constructed to include a c-shaped cross section with a channel defining an interior space for substantially surrounding a portion of the probe, the grip being removable from engagement with the probe, the grip translatable along the cable in the direction of the connector, wherein the interior surface of the body forming the interior space varies along the length of the grip.

5. The probe of claim 4, wherein the interior surface of the body of the grip is tapered.

* * * * *